(12) United States Patent
Smidt et al.

(10) Patent No.: US 8,030,527 B2
(45) Date of Patent: Oct. 4, 2011

(54) PROCESS FOR PREPARING SUBSTITUTED BIPHENYLS

(75) Inventors: Sebastian Peer Smidt, Mannheim (DE); Jochen Dietz, Mannheim (DE); Michael Keil, Freinsheim (DE); Thomas Grote, Wachenheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/726,196

(22) Filed: Mar. 17, 2010

(65) Prior Publication Data

US 2010/0256418 A1    Oct. 7, 2010

Related U.S. Application Data

(62) Division of application No. 12/087,345, filed as application No. PCT/EP2007/055283 on May 31, 2007, now Pat. No. 7,709,684.

(30) Foreign Application Priority Data

Jun. 1, 2006 (EP) .................................. 06114872
Sep. 7, 2006 (EP) .................................. 06120319

(51) Int. Cl.
*C07C 205/06* (2006.01)
(52) U.S. Cl. ........................................ 568/928
(58) Field of Classification Search .................. 568/928
See application file for complete search history.

(56) References Cited

U.S. PATENT DOCUMENTS

| | | | |
|---|---|---|---|
| 6,087,542 A | 7/2000 | Eicken et al. | |
| 6,362,380 B1 | 3/2002 | Eicken et al. | |
| 2003/0100792 A1 | 5/2003 | Koch et al. | |
| 2006/0116414 A1 | 6/2006 | Dunkel et al. | |
| 2008/0183021 A1 | 7/2008 | Engel et al. | |

FOREIGN PATENT DOCUMENTS

| | | |
|---|---|---|
| EP | 1 285 924 A1 | 2/2003 |
| JP | 2001-55360 A | 2/2001 |
| JP | 2003-119175 A | 4/2003 |
| WO | WO-97/33846 A1 | 9/1997 |
| WO | WO-03/070705 A1 | 8/2003 |
| WO | WO 2004/037791 * | 6/2004 |

OTHER PUBLICATIONS

Database CAPLUS on STN, Acc. No. 2004:370906, Nuss et al., WO 2004037791 (May 6, 2004) (abstract).*
Gilbert et al., Tetrahedron Lett., vol. 32, No. 20, 1991, pp. 2277-2280.
Derwent Publ. Ltd., XP-002406829, 2001—347657, pp. 1-3.
Derwent Publ. Ltd., XP-002406830, 2003—498709, pp. 1-3.
Ito et al., Leter, No. 10, 2003, XP 002406825, pp. 1435-1438.
Winkle et al., Organic Process Research & Development, vol. 5, 2001, XP- 002406826, pp. 450-451.
D. G. Hall, "Boronic Acids", Wiley-VCH, pp. 28-32, (2005).

M. F. Hawthorne, "Simple Procedure for the Conversion of Aryl Halides to the Corresponding Phenols", J. Org. Chem., vol. 22, 1957, pp. 1001-1006.
Cole, Organometallics, vol. 11, No. 2, 1992, pp. 653-657.

* cited by examiner

*Primary Examiner* — Brian J Davis
(74) *Attorney, Agent, or Firm* — Birch, Stewart, Kolasch & Birch, LLP

(57) ABSTRACT

A process for preparing substituted biphenyls of the formula I

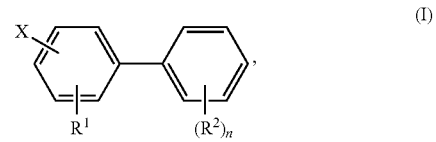

in which the substituents are defined as follows:
X is fluorine or chlorine;
$R^1$ is nitro, amino or $NHR^3$;
$R^2$ is cyano, nitro, halogen, $C_1$-$C_6$-alkyl, $C_1$-$C_6$-alkenyl, $C_1$-$C_6$-alkynyl, $C_1$-$C_6$-alkoxy, $C_1$-$C_6$-haloalkyl, $C_1$-$C_6$-alkylcarbonyl or phenyl;
$R^3$ is $C_1$-$C_4$-alkyl, $C_1$-$C_4$-alkenyl or $C_1$-$C_4$-alkynyl;
n is 1, 2 or 3, where in case that n is 2 or 3, the $R^2$ radicals may also be different,
which comprises reacting the compound of the formula II

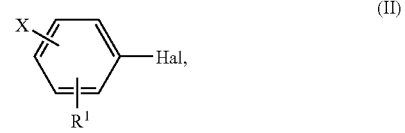

in which Hal is halogen and X and $R^1$ are as defined above, in the presence of a base and of a palladium catalyst selected from the group of:3
a) palladium-triarylphosphine or -trialkylphosphine complex with palladium in the zero oxidation state,
b) salt of palladium in the presence of triarylphospine or trialkylphosphine as a complex ligand or
c) metallic palladium, optionally applied to support, in the presence of triarylphosphine or trialkylphosphine, in a solvent, with a diphenylborinic acid (III)

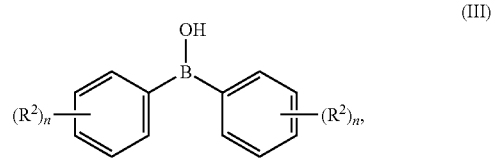

in which $R^2$ and n are as defined above, where the triarylphosphines or trialkylphosphines used may be substituted.

1 Claim, 1 Drawing Sheet

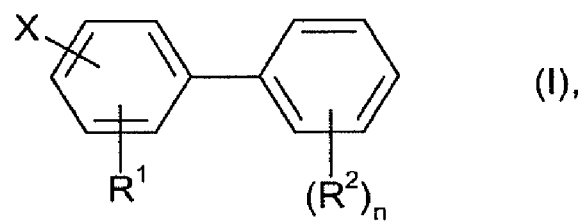
(I),
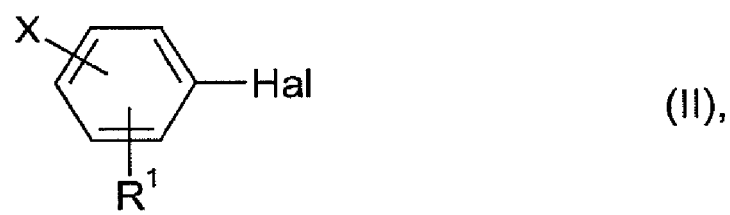
(II),
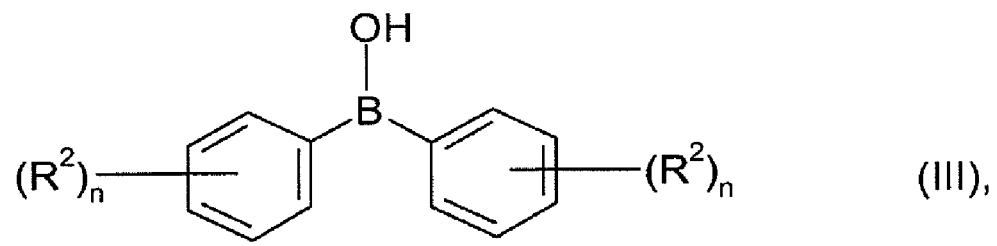
(III),

PROCESS FOR PREPARING SUBSTITUTED BIPHENYLS

The present application is a 37 C.F.R. §1.53(b) divisional of, and claims priority to, U.S. application Ser. No. 12/087,345, filed Jul. 2, 2008 now U.S. Pat. No. 7,709,684. Application Ser. No. 12/087,345 is the national phase under 35 U.S.C. §371 of International Application No. PCT/EP2007/055283, filed on May 31, 2007. Priority is also claimed to European Application 06114872.2 filed on Jun. 1, 2006 and European Application No. 06120319.6 filed on Sep. 7, 2006. The entire contents of each of these applications is hereby incorporated by reference.

DESCRIPTION

The present invention relates to a process for preparing substituted biphenyls of the formula I

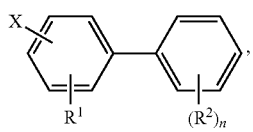

in which the substituents are defined as follows:
X is fluorine or chlorine;
$R^1$ is nitro, amino or $NHR3^-$;
$R^2$ is cyano, nitro, halogen, $C_1$-$C_6$-alkyl, $C_1$-$C_6$-alkenyl, $C_1$-$C_6$-alkynyl, $C_1$-$C_6$-alkoxy, $C_1$-$C_6$-haloalkyl, ($C_1$-$C_6$-alkyl)carbonyl or phenyl;
$R^3$ is $C_1$-$C_4$-alkyl, $C_1$-$C_4$-alkenyl or $C_1$-$C_4$-alkynyl;
n is 1, 2 or 3, where in case that n is 2 or 3, the $R^2$ radicals may also be different, which comprises reacting a compound of formula 11

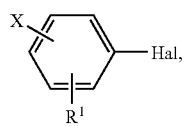

in which Hal is halogen and X and $R^1$ are as defined above, in the presence of a base and of a palladium catalyst selected from the group of:
a) palladium-triarylphosphine or -trialkylphosphine complex with palladium in the zero oxidation state,
b) salt of palladium in the presence of triarylphospine or trialkylphosphine as a complex ligand or
c) metallic palladium, optionally applied to support, in the presence of triarylphosphine or trialkylphosphine, in a solvent, with a diphenylborinic acid (III)

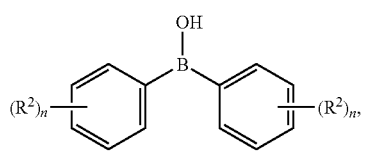

in which $R^1$ and n are as defined above, where the triarylphosphines or trialkylphosphines used may be substituted.

Tetrahedron Lett. 32, page 2277 (1991) states that the coupling reaction between phenylboronic acid and chlorobenzene with use of the [1,4-bis(diphenylphosphine)-butane]palladium(II) dichloride catalyst proceeds with a yield of only 28%.

EP-A 0 888 261 discloses a process for preparing nitrobiphenyls by reacting chloronitrobenzenes with a phenylboronic acid in the presence of a palladium catalyst and of a base. In this process, a very high catalyst concentration is necessary.

It was therefore an object of the present invention to provide an economically viable process which can be implemented on the industrial scale for regioselectively preparing substituted biphenyls, which works with a reduced palladium catalyst concentration.

Accordingly, the process defined at the outset has been found.

BRIEF DESCRIPTION OF THE DRAWINGS

The FIGURE depicts the substituted biphenyl of formula (I) and the halogen-containing compound of formula (II) and the diphenylborinic acid (III).

DETAILED DESCRIPTION OF THE INVENTION

The diphenylborinic acid (III) is obtained by reaction of optionally substituted phenylmagnesium chloride V with trialkyl borate, preferably trimethyl borate, in tetrahydrofuran as a solvent according to scheme 1 which follows.

Scheme 1:

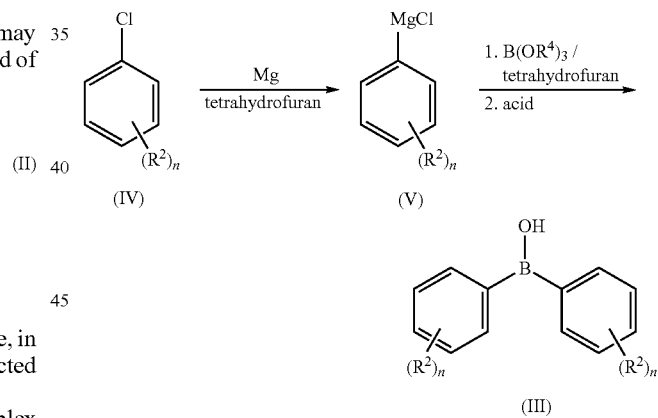

$R^4$ is $C_1$—$C_4$-alkyl, preferably methyl.

Essential for a high yield of diphenylborinic acid (III) is the use of only 0.7 eq. of trialkyl borate based on the substituted chlorobenzene (IV) used. Use of 1.1 eq. of trialkyl borate gives rise to phenylboronic acid as described in EP-A 0 888 261.

This reduction in the trialkyl borate use has several surprising advantages in relation to the preparation of nitrobiphenyls (I). The space-time yield is increased. The feedstock costs are lowered as a result of reduction in the amount of expensive trimethyl borate. Unlike the phenylboronic acids used in EP-A 0 888 261, the diphenylborinic acids (III) are soluble in tetrahydrofuran, which leads to an improvement in heat removal during the reaction, which is accompanied by lower consumption of the cooling capacity. This leads in turn to higher process safety.

The reaction temperature in this process stage is from 10 to 30° C., preferably from 15 to 25° C.

The substituted biphenyls prepared by the present process have the following preferred substituents, in each case both individually and in combination:

$R^1$ nitro, amino, methylamino, propylamino, butylamino, allylamino or propargylamino, more preferably nitro, amino or methylamino, most preferably nitro or amino;

$R^2$ cyano, nitro, fluorine, chlorine, bromine, methyl, ethyl, propyl, butyl, allyl, propargyl, methoxy, ethoxy, trifluoromethyl or phenyl, more preferably fluorine, chlorine, methyl or methoxy, most preferably fluorine or chlorine;

$R^3$ methyl, ethyl, propyl, butyl, allyl or propargyl, more preferably methyl, ethyl or allyl, most preferably methyl;

n 1 or 2, preferably 2.

The subsequent homogeneously catalyzed Suzuki biaryl cross-coupling is carried out according to scheme 2.

Scheme 2:

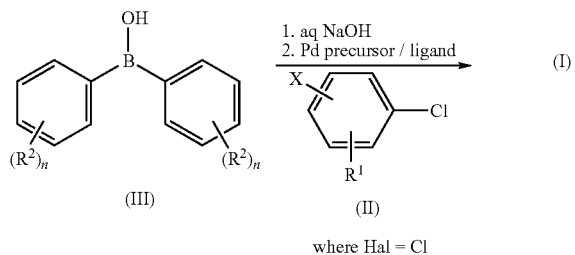

where Hal = Cl

Preference is given to starting from diphenylborinic acids of the formula (III) in which $R^2$ and n are as defined above.

Further preferred starting materials are diphenylborinic acids (III) in which n is 1 or 2, in particular 2. Particularly preferred are diphenylborinic acids (III) which are substituted in the 3- and 4-position.

Very particular preference is given to di(2,3-difluorophenyl)borinic acid, di(3,4-difluorophenyl)borinic acid, di(2,3-dichlorophenyl)borinic acid and in particular di(3,4-dichlorophenyl)borinic acid as the starting compound (III).

Preference is given to starting from the following compounds (II):

2-bromo-4-fluoroaniline, 2-chloro-4-fluoroaniline and in particular 2-chloro-4-fluoro-1-nitrobenzene or 2-bromo-4-fluoro-1-nitrobenzene.

The compound (II) is used, based on the diphenylborinic acids (III) (diphenylborinic acid equivalents), normally in an equimolar amount, preferably with an up to 20 percent excess, in particular with an up to 50 percent excess.

The bases used may be organic bases, for example tertiary amines. Preference is given to using, for example, triethylamine or dimethylcyclohexylamine.

The bases used are preferably alkali metal hydroxides, alkaline earth metal hydroxides, alkali metal carbonates, alkaline earth metal carbonates, alkali metal hydrogen-carbonates, alkali metal acetates, alkaline earth metal acetates, alkali metal alkoxides and alkaline earth metal alkoxides, in a mixture and in particular individually.

Particularly preferred bases are alkali metal hydroxides, alkaline earth metal hydroxides, alkali metal carbonates, alkaline earth metal carbonates and alkali metal hydrogencarbonates.

Especially preferred bases are alkali metal hydroxides, e.g. sodium hydroxide and potassium hydroxide, and also alkali metal carbonates and alkali metal hydrogencarbonates, e.g. lithium carbonate, sodium carbonate and potassium carbonate.

The base is used in the process according to the invention preferably with a fraction of from 100 to 500 mol %, more preferably from 150 to 400 mol %, based on the amount of diphenylborinic acid (III).

Suitable palladium catalysts are palladium-ligand complexes with palladium in the zero oxidation state, salts of palladium in the presence of complex ligands, or metallic palladium optionally applied to support, preferably in the presence of complex ligands.

Suitable complex ligands are uncharged ligands such as triarylphosphines and trialkylphosphines, which may optionally be substituted in the aryl rings, such as triphenylphosphine (TPP), di-1-adamantyl-n-butylphosphine, tri-tert-butylphosphine (TtBP) or 2-(dicyclohexylphosphino)biphenyl.

Furthermore, the literature has also described further particularly reactive complex ligands from other structural classes, including 1,3-bis(2,6-diisopropylphenyl)-4,5-H2-imidazolium chloride (cf., for example, G. A. Grasa et al. Organometallics 2002, 21, 2866) and tris(2,4-di-tert-butylphenyl) phosphite (cf. A. Zapf et al., Chem. Eur. J. 2000, 6, 1830).

The reactivity of the complex ligands can be enhanced by adding a quaternary ammonium salt such as tetra-n-butylammonium bromide (TBAB) (cf., for example, D. Zim et al., Tetrahedron Lett. 2000, 41, 8199).

If required, the water solubility of the palladium complexes can be improved by various substituents such as sulfonic acid or sulfonate salt groups, carboxylic acid or carboxylate salt groups, phosphonic acid, phosphonium or phosphonate salt groups, peralkylammonium, hydroxyl and polyether groups.

Among the palladium-ligand complexes with palladium in the 0 oxidation state, preference is given to using tetrakis (triphenylphosphine)palladium and additionally tetrakis [tri (o-tolyl)phosphine]palladium.

In the salts of palladium which are used in the presence of complex ligands, the palladium is normally present in the two positive oxidation state. Preference is given to using palladium chloride, palladium acetate or bisacetonitrilepalladium chloride. Particular preference is given to using palladium chloride.

In general, from 6 to 60, preferably from 15 to 25, equivalents of the aforementioned complex ligands, in particular triphenylphosphine and tri-tert-butylphosphine, are combined with one equivalent of the palladium salt.

EP-A 0 888 261 describes the use of from 2 to 6 equivalents of triphenylphosphine per equivalent of the palladium catalyst. The use of high ligand excesses is generally viewed in the literature as disadvantageous, since this is expected to result in inactivation of the catalytically active complex (cf., for example, J. Hassan et al., Chem. Rev. 2002, 102, 1359).

It was thus surprising that this high triphenylphosphine use in combination with the low catalyst use led to an increase in the overall yield of the process of the present invention and accordingly to an improvement in the economic viability.

Metallic palladium is used preferably in pulverized form or on a support material, for example in the form of palladium on activated carbon, palladium on alumina, palladium on barium carbonate, palladium on barium sulfate, palladium on calcium carbonate, palladium aluminosilicates such as montmorillonite, palladium on $SiO_2$ and palladium on calcium carbonate, in each case with a palladium content of from 0.5 to 12% by weight. In addition to palladium and the support material, these catalyst may comprise further dopants, for example lead.

When metallic palladium optionally applied to support is used, particular preference is given to also using the aforementioned complex ligands, in particular to the use of palladium on activated carbon in the presence of triphenylphosphine as a complex ligand, where the phenyl groups in the triphenylphosphine are preferably substituted by a total of from one to three sulfonate groups.

In the process according to the invention, the palladium catalyst is used with a low fraction of from 0.001 to 1.0 mol %, preferably from 0.005 to 0.5 mol % or from 0.01 to 0.5 mol % and in particular from 0.005 to 0.05 mol %, based on the amount of compound (II).

The low use of a palladium salt in combination with a high use of a complex ligand constitutes a significant cost advantage of this process over the prior art processes.

The process according to the invention may be carried out in a biphasic system composed of aqueous phase and solid phase, i.e. the catalyst. In that case, the aqueous phase may also comprise a water-soluble organic solvent in addition to water.

Organic solvents suitable for the process according to the invention are ethers such as dimethoxyethane, diethylene glycol dimethyl ether, tetrahydrofuran, dioxane and tert.-butyl methyl ether, hydrocarbons such as n-hexane, n-heptane, cyclohexane, benzene, toluene and xylene, alcohols such as methanol, ethanol, 1-propanol, 2-propanol, ethylene glycol, 1-butanol, 2-butanol and tert.-butanol, ketones such as acetone, ethyl methyl ketone and isobutyl methyl ketone, amides such as dimethylformamide, dimethylacetamide and N-methylpyrrolidone, in each case individually or in a mixture.

Preferred solvents are ethers such as dimethoxyethane, tetrahydrofuran and dioxane, hydrocarbons such as cyclohexane, toluene and xylene, alcohols such as ethanol, 1-propanol, 2-propanol, 1-butanol and tert.-butanol, in each case individually or in a mixture.

In a particularly preferred variant of the process according to the invention, water, one or more water-insoluble and one or more water-soluble solvents are used, for example mixtures of water and dioxane, or water and tetrahydrofuran, or water, dioxane and ethanol, or water, tetrahydrofuran and methanol, or water, toluene and tetrahydrofuran, preferably water and tetrahydrofuran, or water, tetrahydrofuran and methanol.

The total amount of solvent is normally from 3000 to 500 g and preferably from 2000 to 700 g, per mole of the compound (II).

Appropriately, the process is carried out by adding the compound (II), the diphenyl-borinic acids (III), the base and the catalytic amount of the palladium catalyst to a mixture of water and one or more inert organic solvents, and stirring at a temperature of from 50° C. to 120° C., preferably from 70° C. to 110° C., more preferably from 90° C. to 100° C., for a period of from 1 to 50 hours, preferably from 2 to 24 hours.

Depending on the solvent and temperature used, a pressure of from 1 bar to 6 bar, preferably from 1 bar to 4 bar, is established.

Preference is given to carrying out the reaction in water and tetrahydrofuran.

The reaction may be carried out in customary apparatus suitable for such processes.

On completion of reaction, palladium catalyst obtained as a solid is removed, for example by filtration, and the crude product is freed from the solvent or the solvents.

In the case of products which are not fully water-soluble, water-soluble palladium catalysts or complex ligands are removed fully from the crude product in the separation of the water phase.

Subsequently, further purification may be effected by methods which are known to those skilled in the art and are appropriate to the particular product, for example by recrystallization, distillation, sublimation, zone melting, melt crystallization or chromatography.

By the process according to the invention, it is possible to prepare, for example:
3',4'-dichloro-5-fluoro-biphenyl-2-ylamine,
2',3'-dichloro-5-fluoro-biphenyl-2-ylamine,
3',4'-dichloro-3-fluoro-biphenyl-2-ylamine,
2',3'-dichloro-3-fluoro-biphenyl-2-ylamine,
3',4'-dichloro-4-fluoro-biphenyl-2-ylamine,
2',3'-dichloro4-fluoro-biphenyl-2-ylamine,
3',4'-dichloro-6-fluoro-biphenyl-2-ylamine,
2',3'-dichloro-6-fluoro-biphenyl-2-ylamine,
3',4'-difluoro-5-fluoro-biphenyl-2-ylamine,
2',3'-difluoro-5-fluoro-biphenyl-2-ylamine,
3',4'-difluoro-3-fluoro-biphenyl-2-ylamine,
2',3'-difluoro-3-fluoro-biphenyl-2-ylamine,
3',4'-difluoro-4-fluoro-biphenyl-2-ylamine,
2',3'-difluoro-4-fluoro-biphenyl-2-ylamine,
3',4'-difluoro-6-fluoro-biphenyl-2-ylamine,
2',3'-dichloro-6-fluoro-biphenyl-2-ylamine,
3',4'-dichloro-5-chloro-biphenyl-2-ylamine,
2',3'-dichloro-5-chloro-biphenyl-2-ylamine,
3',4'-dichloro-3-chloro-biphenyl-2-ylamine,
2',3'-dichloro-3-chloro-biphenyl-2-ylamine,
3',4'-dichloro-4-chloro-biphenyl-2-ylamine,
2',3'-dichloro-4-chloro-biphenyl-2-ylamine,
3',4'-dichloro-6-chloro-biphenyl-2-ylamine,
2',3'-dichloro-6-chloro-biphenyl-2-ylamine,
3',4'-di fluoro-5-chloro-biphenyl-2-ylamine,
2',3'-difluoro-5-chloro-biphenyl-2-ylamine,
3',4'-difluoro-3-chloro-biphenyl-2-ylamine,
2',3'-difluoro-3-chloro-biphenyl-2-ylamine,
3',4'-difluoro-4-chloro-biphenyl-2-ylamine,
2',3'-difluoro-4-chloro-biphenyl-2-ylamine,
3',4'-difluoro-6-chloro-biphenyl-2-ylamine,
2',3'-dichloro-6-chloro-biphenyl-2-ylamine,
3',4'-dichloro-5-fluoro-2-nitrobiphenyl,
2',3'-dichloro-5-fluoro-2-nitrobiphenyl,
3',4'-dichloro-3-fluoro-2-nitrobiphenyl,
2',3'-dichloro-3-fluoro-2-nitrobiphenyl,
3',4'-dichloro-4-fluoro-2-nitrobiphenyl,
2',3'-dichloro-4-fluoro-2-nitrobiphenyl,
3',4'-dichloro-6-fluoro-2-nitrobiphenyl,
2',3'-dichloro-6-fluoro-2-nitrobiphenyl,
3',4'-difluoro-5-fluoro-2-nitrobiphenyl,
2',3'-difluoro-5-fluoro-2-nitrobiphenyl,
3',4'-difluoro-3-fluoro-2-nitrobiphenyl,
2',3'-difluoro-3-fluoro-2-nitrobiphenyl,
3',4'-difluoro-4-fluoro-2-nitrobiphenyl,
2',3'-difluoro-4-fluoro-2-nitrobiphenyl,
3',4'-difluoro-6-fluoro-2-nitrobiphenyl,
2',3'-dichloro-6-fluoro-2-nitrobiphenyl,
3',4'-dichloro-5-chloro-2-nitrobiphenyl,
2',3'-dichloro-5-chloro-2-nitrobiphenyl,
3',4'-dichloro-3-chloro-2-nitrobiphenyl,
2',3'-dichloro-3-chloro-2-nitrobiphenyl,
3',4'-dichloro-4-chloro-2-nitrobiphenyl,
2',3'-dichloro-4-chloro-2-nitro biphenyl,
3',4'-dichloro-6-chloro-2-nitrobiphenyl,
2',3'-dichloro-6-chloro-2-nitrobiphenyl, 3',4'-difluoro-5-chloro-2-nitrobiphenyl,
2',3'-difluoro-5-chloro-2-nitrobiphenyl,
3',4'-difluoro-3-chloro-2-nitrobiphenyl,
2',3'-difluoro-3-chloro-2-nitrobiphenyl,
3',4'-difluoro-4-chloro-2-nitrobiphenyl,
2',3'-difluoro-4-chloro-2-nitrobiphenyl,
3',4'-difluoro-6-chloro-2-nitrobiphenyl,
2',3'-dichloro-6-chloro-2-nitrobiphenyl.

The process according to the invention affords the compounds I in very high up to quantitative yields at very good purity.

The substituted biphenyls obtainable by the process according to the invention are suitable as precursors for fungicidal crop protection active ingredients (cf. WO 03/070705).

Synthesis of 3',4'-dichloro-5-fluoro-2-nitro-biphenyl

EXAMPLE 1

Di-(3,4-dichlorophenyl)borinic acid

A solution of 12.81 g of trimethyl borate (123 mM) and 30 mL of tetrahydrofuran is heated to reflux. To this are metered 245 g of a 18% by weight solution of 3,4-dichlorophenylmagnesium bromide (177 mM) in tetrahydrofuran within 1 hours. After full addition, the reaction solution is stirred at reflux for another hour.

The reaction solution is subsequently treated with 110 mL of 10% aqueous hydrochloric acid and stirred at 40° C. for 30 minutes. After phase separation, a solution of di(3,4-dichlorophenyl)borinic acid in tetrahydrofuran is obtained. 32.1 g of di(4-chlorophenyl)borinic acid is isolated by crystallization from 200 mL of hexane (yield 57%). MS: m/z=320 $[m+H]^+$, $^1$H-NMR (DMSO, 500 MHz): δ [ppm]=7.51 (s, 1H), 7.38 (d, 1H, 7 Hz), 7.27 (d, 1H, 7 Hz).

EXAMPLE 2

Reaction of di(3,4-dichlorophenyl)borinic acid and 2-bromo-4-fluoro-aniline

A reaction flask is initially charged with 0.55 g of sodium hydroxide (13.7 mM) and 50 mL of water at 15-20° C.

To this are metered 2.5 g of di(3,4-dichlorophenyl)borinic acid (7.8 mM) and 0.199 g of triphenylphosphine (0.76 mM) in 50 mL of dioxane. After full addition, the reaction solution is stirred at 18-22° C. for 40 minutes. After deoxygenation, 27 mg of palladium(II) chloride (0.15 mM) and 1,4 g of 2-bromo-4-fluoro-aniline (7.4 mM) are added to the reaction solution. The reaction solution is heated to 85° C. for 6 hours. The reaction mixture is cooled down, acidified with 2 M hydrochloric acid and the dioxane evaporated. The residue is extracted with dichloromethane and after evaporation of solvent the 3',4'-dichloro-5-fluoro-biphenyl-2-ylamine is isolated by column chromatography (0.63 g, yield 33%).

HPLC-MS: m/z=256.0 $[m+H]^+$

EXAMPLE 3

Reaction of di(3,4-dichlorophenyl)borinic acid and 2-chloro-4-fluoro-1-nitro-benzene A reaction flask is initially charged with 0.55 g of sodium hydroxide (13.7 mM) and 50 mL of water at 15-20° C.

To this are metered 2.5 g of di(3,4-dichlorophenyl)borinic acid (7.8 mM) and 0.199 g of triphenylphosphine (0.76 mM) in 50 mL of dioxane. After full addition, the reaction solution is stirred at 18-22° C. for 40 minutes. After deoxygenation, 27 mg of palladium(II) chloride (0.15 mM) and 1.3 g of 2-chloro-4-fluoro-1-nitro-benzene (7.4 mM) are added to the reaction solution. The reaction solution is heated to 85° C. for 6 hours.

The reaction mixture is cooled down, acidified with 2 M hydrochloric acid and the dioxane evaporated. The residue is extracted with dichloromethane and after evaporation of solvent the 3',4'-dichloro-5-fluoro-2-nitro-biphenyl is isolated by column chromatography (0.76 g, yield 36%).

GC-MS: m/z=285.9 $[m-H]^-$

What is claimed is:
1. The compound 3',4'-dichloro-5-fluoro-2-nitrobiphenyl.

* * * * *